United States Patent [19]

Noon et al.

[11] Patent Number: 4,634,466
[45] Date of Patent: Jan. 6, 1987

[54] TRIAZOLES AND USE AS FUNGICIDES AND PLANT GROWTH REGULATORS

[75] Inventors: Robert A. Noon, Maidenhead; Patrick J. Crowley, Crowthorne; Diana M. Worthington, Maidenhead, all of England

[73] Assignee: Imperial Chemical Industries PLC, London, England

[21] Appl. No.: 499,399

[22] Filed: May 31, 1983

[30] Foreign Application Priority Data

Jun. 14, 1982 [GB] United Kingdom ............... 8217206
Jun. 18, 1982 [GB] United Kingdom ............... 8217693
Jan. 21, 1983 [GB] United Kingdom ............... 8301679

[51] Int. Cl.$^4$ .................. A01N 43/653; C07D 249/08
[52] U.S. Cl. ......................................... 71/92; 71/76; 514/184; 514/383; 514/399; 548/101; 548/262; 548/341; 549/563; 568/663; 568/812
[58] Field of Search ............... 548/101, 262; 424/245, 424/269; 71/76, 92; 514/184, 383

[56] References Cited

U.S. PATENT DOCUMENTS 4,414,210 11/1983 Miller et al. ................... 548/262

FOREIGN PATENT DOCUMENTS 040345 11/1981 European Pat. Off. .
0052424 5/1982 European Pat. Off. ............ 424/269
060223 9/1982 European Pat. Off. .

Primary Examiner—Richard L. Raymond
Attorney, Agent, or Firm—Cushman, Darby & Cushman

[57] ABSTRACT

A compound having the formula:

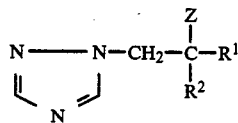

and stereoisomers thereof, wherein $R^1$ is —CH=CH—X or —C≡C—X where X is hydrogen or straight chain alkyl; $R^2$ is halophenyl, Z is $OR^3$ where $R^3$ is H, alkyl, alkenyl or aklynyl; and acid addition salts and metal complexes thereof. The compounds are characterized by their fungicidal and plant growth activity.

8 Claims, No Drawings

TRIAZOLES AND USE AS FUNGICIDES AND PLANT GROWTH REGULATORS

This invention relates to triazole and imidazole compounds useful as fungicides, to processes for preparing them, to fungicidal and plant growth regulating compositions containing them, and to a method of combating fungal infections in plants using them; and to a method of regulating plant growth using them.

In European Patent Application No 81304835.2 there are disclosed, and claimed triazole and imidazole compounds having the general formula:

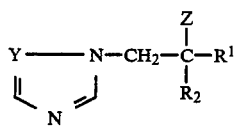

wherein $R^1$ is —CH=CH—X, —C≡C—X or —CH$_2$—CH$_2$—X where X is H, alkyl, hydroxyalkyl, alkoxyalkyl, cycloalkyl or optionally substituted aryl, aralkyl, aryloxy, alkyl, or heterocyclyl; and $R^2$ is alkyl, cycloalkyl (e.g. cyclopropyl, cyclopentyl, or cyclohexyl) or optionally substituted aryl; Z is Cl or CN or $OR^3$ where $R^3$ is H, acetyl, alkyl, alkenyl or aralkyl; Y is =N— or =CH—; and acid addition salts and metal complexes thereof.

We have now found that a certain, narrow, class of compounds within the broad generic group defined above have an appreciably higher degree of fungicidal activity.

According to the present invention, therefore, there are provided triazole compounds having the formula:

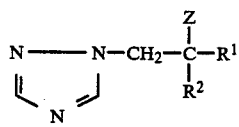

wherein $R^1$ is —CH=CH—X or —C≡C—X where X is hydrogen or straight chain alkyl containing from 1 to 5 carbon atoms; $R^2$ is halophenyl; Z is $OR^3$ where $R^3$ is H, alkyl, alkenyl or alkynyl; and acid addition salts and metal complexes thereof.

The compounds of the invention can contain geometric isomers. Such compounds are generally obtained in the form of isomeric mixtures. However, these and other mixtures can be separated into the individual isomers by methods known in the art.

When X is an alkyl group it is a straight chain group having 1 to 5 carbon atoms; examples are methyl, ethyl, propyl, butyl and amyl. Otherwise, that is for $R^3$, as appropriate, the alkyl group can be a straight or branched chain group having from 1 to 6, for example from 1 to 4, carbon atoms; examples are methyl, ethyl, propyl (n- or iso-propyl) and butyl (n-, sec-, iso- or t-butyl). When $R^2$ is halophenyl examples of suitable halogens as substituents for the phenyl ring are fluorine, chlorine or bromine. Thus $R^2$ may be 2-, 3- or 4-chlorophenyl, 2,4- or 2,6-dichlorophenyl, 2-, 3- or 4-fluorophenyl, 2,4-difluorophenyl, 2-, 3- or 4-bromophenyl, 2-chloro-4-fluorophenyl, or 2-chloro-6-fluorophenyl.

$R^2$ is preferably 4-chlorophenyl or 2,4-dichlorophenyl.

In a further aspect, therefore, the invention provides a compound as defined above wherein X is H or $C_{1-4}$ alkyl; $R^2$ is 4-chlorophenyl or 2,4-dichlorophenyl; and Z is $OR^3$ where $R^3$ is H.

In an even further preferred aspect the invention provides a compound as defined above wherein $R^2$ is 2-, 4- or 2,4-dichloro- or difluorophenyl.

Preferred compounds have the formula:

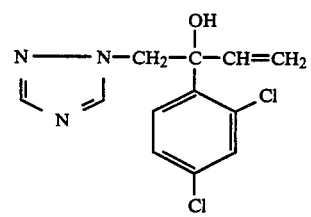

and

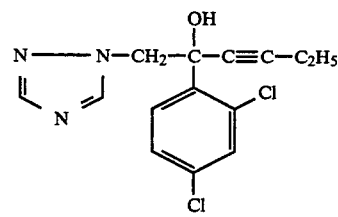

The salts can be salts with inorganic or organic acids eg. hydrochloric, nitric, sulphuric, acetic, 4-toluene sulphonic or oxalic acid.

Suitably the metal complex is one including, as the metal, copper, zinc, manganese or iron. It preferably has the general formula:

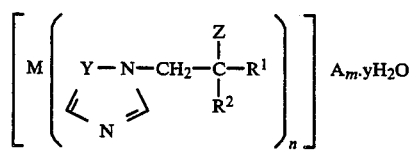

wherein $R^1$ and $R^2$, Z and Y are as defined above, M is a metal, A is an anion (eg. a chloride, bromide, iodide, nitrate sulphate or phosphate anion), n is 2 or 4, y is 0 or an integer of 1 to 12, and m is an integer consistent with valency.

Examples of the compounds of the invention are shown in Table I. These compounds correspond to the general formulae:

TABLE I

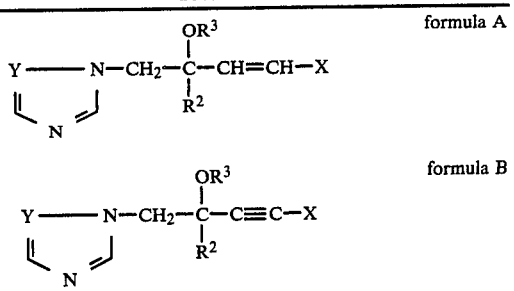

formula A formula B

| COMPOUND NO | FORMULA | R³ | X | R² | Y | MELTING POINT °C. |
|---|---|---|---|---|---|---|
| 1 | B | H | n-C₃H₇ | 2,4-dichlorophenyl | N | 83–85 |
| 2 | B | H | C₂H₅ | 2,4-dichlorophenyl | N | 129–130 |
| 3 | A | H | n-C₃H₇ | 2,4-dichlorophenyl | N | 94–95 |
| 4 | A | H | C₂H₅ | 2,4-dichlorophenyl | N | 109–110 |
| 5 | A | H | H | 2,4-dichlorophenyl | N | 88–90 |
| 6 | B | H | H | 2,4-dichlorophenyl | N | 129–131 |
| 7 | B | H | CH₃ | 2,4-dichlorophenyl | N | 145–147 |
| 8 | B | H | C₂H₅ | 2,4-difluorophenyl | N | 76–78 |
| 9 | B | H | C₂H₅ | 4-chlorophenyl | N | glass: b.p. 140–200 at 0.01 millibar |
| 10 | B | H | H | 4-chlorophenyl | N | |
| 11 | A | H | H | 2,4-difluorophenyl | N | 103–104 |
| 12 | A | H | H | 4-chlorophenyl | N | 80–83 |
| 13 | B | CH₃ | C₂H₅ | 2,4-dichlorophenyl | N | Viscous Oil |
| 14 | B | H | C₅H₁₁ | 2,4-dichlorophenyl | N | 83–84 |
| 15 | A | H | C₅H₁₁ | 2,4-dichlorophenyl | N | 58–61 |

In the foregoing Table the compounds are novel and as such they therefore form part of the present invention.

The compounds of general formula (I) may be produced by reacting a compound of general formula (II) or (III):

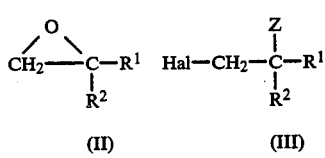

in which R¹, R² and Z are as defined above and Hal is a halogen atom (preferably a chlorine or bromine atom), with 1,2,4-triazole or imidazole either in the presence of an acid-binding agent or in the form of one of its alkali metal salts in a convenient solvent.

Suitably the compound of general formula (II) or (III) is reacted at 20°–100° C. with the sodium salt of 1,2,4-triazole or imidazole (the salt can be prepared by adding either sodium hydride or sodium methoxide to 1,2,4-triazole or imidazole) in a convenient solvent such as acetonitrile, methanol, ethanol or dimethylformamide. The product can be isolated by pouring the reaction mixture into water and recrystallising the solid formed from a convenient solvent.

The ethers (R₃=alkyl etc) of the invention are made from the hydroxy compounds by reacting them with the appropriate halide in the presence of a suitable base.

The compounds of general formula (II) wherein each of R¹ and R² are as defined above are novel and useful intermediates and, per se, form part of the present invention. They can be prepared by reacting the appropriate compound of general formula (IV)

$$R^1-CO-R^2 \qquad (IV)$$

wherein R¹ and R² are as defined above, with dimethylsulphonium methylide (Corey and Chaykovsky, JACS, 1962, 84, 3782) or dimethyl oxosulphonium methylide (Corey and Chaykovsky, JACS, 1965, 87, 1353–1364) using methods set out in the literature.

The α,β-unsaturated ketones of general formula (V) can be made by condensing the appropriate ketones and aldehydes in the presence of suitable acid or base catalysts

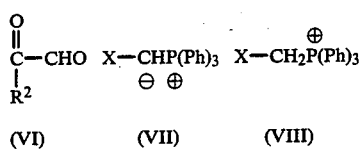

(V)

They can also be made by Wittig reactions between aldehydes of structure (VI) and phosphoranes of structure (VII):

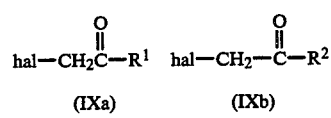

(VI)   (VII)   (VIII)

where R² and X are as defined above.

The phosphoranes (VII) are derived from the phosphonium salts (VIII) by treatment with a strong base such as n-butyl lithium in a suitable solvent such as ether or tetrahydrofuran according to standard methods in the literature. The aldehydes (VI) can be made by methods set out in the literature.

The compounds of general formula (II) and (III) wherein Z is OH can also be prepared by reacting a compound of general formula (IXa) or (IXb)

(IXa)   (IXb)

wherein R¹, R² and hal are as defined above, with an organometallic compound of general formula (Xa) or (Xb)

R¹M   R²M (Xa)   (Xb)

wherein R¹ and R² are as defined above and M is a metal which is preferably lithium, but which may be sodium or magnesium (when M is magnesium the organo metallic compound is actually R¹Mghal or R²Mghal) in a convenient solvent such as diethyl ether or tetrahydrofuran. The reaction may give only (III) or only (II) or a mixture of (II) and (III). Preferably (Xa) is reacted with (IXb) at low temperature.

The compounds of general formula (IX) and (X) may be made by methods set out in the literature, For example the acetylenic alcohols of the invention can be made by either of the following two schemes 1 and 2.

SCHEME 1

α-halo ketones of the general formula (IXb) shown below, and wherein R₂ is as defined above are brought into reaction with a metal salt of the appropriate acetylene of general formula (XI) wherein X is as defined above, in an inert atmosphere at low temperature and working up the product by quenching with a proton donor.

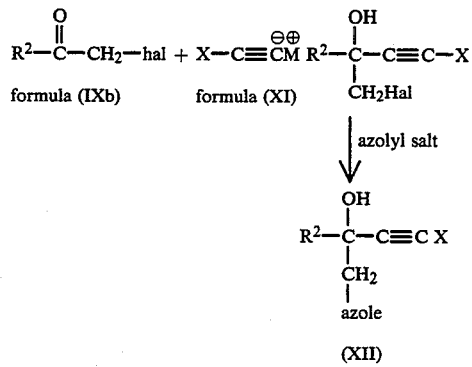

SCHEME 2

An acetylenic ketone of general formula (XIII) is brought into reaction with a sulphur ylid of general formula (XIV) and the resultant epoxide is brought into reaction with the appropriate azolyl salt.

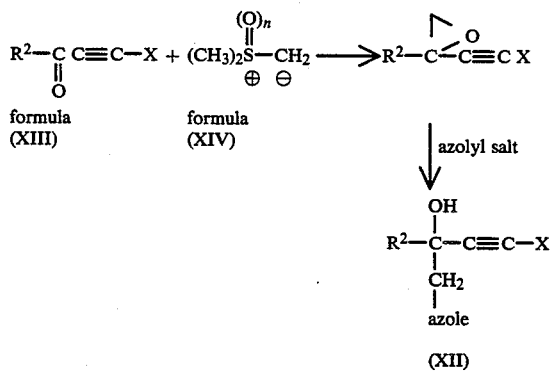

The salts and metal complexes of the compounds of general formula (I) can be prepared from the latter in known manner. For example, the complexes can be made by reacting the uncomplexed compound with a metal salt in a suitable solvent.

The olefinic azolyl alcohols, where R¹ is CH=CH—X and R² is as defined above can also be made by reduction of the acetylenic azolyl alcohols (XII), using either hydrogen in the presence of a suitable catalyst such as palladium on carbon (or other supports), or a metal hydride reagent especially lithium aluminium hydride in a suitable solvent such as ether or tetrahydrofurnan.

SCHEME 3

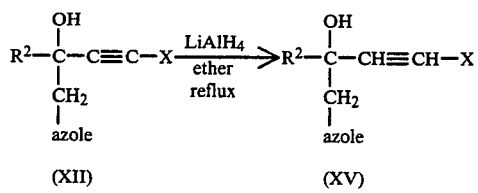

An acetylenic azolyl alcohol of general formula (XII) is brought into reaction with a metal hydride reagent to produce the invention compounds of formula (XV).

The compounds, salts and metal complexes are active fungicides, particularly against the diseases:

*Piricularia oryzae* on rice

*Puccinia recondita, Puccinia striiformis* and other rusts on wheat, *Puccinia hordei, Puccinia striiformis* and other rusts on barley, and rusts on other hosts e.g. coffee, apples, apples, vegetables and ornamental plants

*Erysiphe graminis* (powdery mildew) on barley and wheat and other powdery mildews on various hosts such as

*Sphaerotheca fuliginea* on cucurbits (e.g. cucumber),

*Podosphaera leucotricha* on apples and *Uncinula necator* on vines

*Helminthosporium* spp., *Rhynchosporium* spp. and *Pseudocercosporella herpotrichoids* on cereals

*Cercospora arachidicola* on peanuts and other *Cercospora* species on for example sugar beet, bananas and soya beans

*Botrytis cinerea* (grey mould) on tomatoes, strawberries, vines and other hosts

*Ventruia inaequalis* (scab) on apples

Some of the compounds have also shown a broad range of activities against fungi in vitro. They have activity against various post-harvest diseases on fruit (e.g. *Penicillium digatatum* and *italicum* on oranges and *Gloeosporium musarum* on bananas). Further some of the compounds are active as seed dressings against: Fusarium spp., Septoria spp., Tilletia spp. (i.e. bunt, a seed borne disease of wheat), Ustilago spp., Helminthosporium spp. and *Pseudocercosporella herpotrichloides* on cereals, *Rhizoctonia solani* on cotton and *Corticium sasakii* on rice.

The compounds can move acropetally in the plant tissue. Moreover, the compounds can be volatile enough to be active in the vapour phase against fungi on the plant.

They may also be useful as industrial (as opposed to agricultural) fungicides, e.g. in the prevention of fungal attack on wood, hides, leather and especially paint films.

The compounds are also useful for the treatment of candidiasis and human dermatophyte infections.

The compounds, and their derivatives as defined above, also have plant growth regulating activities.

The plant growth regulating effects of the compounds are manifested as for example a stunting or dwarfing effect on the vegetative growth of woody and herbaceous mono- and di-cotyledonous plants. Such stunting or dwarfing may be useful, for example, in peanuts, cereals such as wheat and barley, oil seed rape, field beans, sunflowers, potatoes and soya bean where reduction in stem height, with or without further advantageous effects such as stem strengthening, thickening and shortening, internode shortening, increased buttress root formation and more erect stem and leaf orientation, may reduce the risk of lodging and may also permit increased amounts of fertiliser to be applied. The stunting of woody species is useful in controlling the growth of undergrowth under power lines etc. Compounds which induce stunting or dwarfing may also be useful in modifying the stem growth of sugar cane thereby increasing the concentration of sugar in the cane at harvest; in sugar cane, the flowering and ripening may be controllable by applying the compounds. Stunting of peanuts can assist in harvesting. Growth retardation of grasses can help maintenance of grass swards. Examples of suitable grasses are *Stenotaphrum secundatum* (St. Augustine grass), *Cynosurus cristatus, Lolium multiflorum* and *perenne, Agrostis tenuis, Cynodon dactylon* (Bermuda grass), *Dactylis glomerata*, *Festuca* spp. (e.g. *Festuca rubra*) and *Poa* spp. (e.g. *Poa pratense*). The compounds may stunt grasses without significant phytotoxic effects and without deleteriously affecting the appearance (particularly the colour) of the grass; this makes such compounds attractive for use on ornamental lawns and on grass verges. They may also have an effect on flower head emergence in for example grasses. The compounds can also stunt weed species present in the grasses; examples of such weed species are sedges (e.g. Cyperus spp.) and dicotyledonous weeds (e.g. daisy, plantain, knotweed, speedwell, thistle, docks and ragwort). The growth of non-crop vegetation (eg. weeds or cover vegetation) can be retarded thus assisting in the maintenance of plantation and field crops. In fruit orchards, particularly orchards subject to soil erosion, the presence of grass cover is important. However excessive grass growth requires substantial maintenance. The compounds of the invention could be useful in this situation as they could restrict growth without killing the plants which would lead to soil erosion; at the same time the degree of competition for nutrients and water by the grass would be reduced and this could result in an increased yield of fruit. In some cases, one grass species may be stunted more than another grass species; this selectivity could be useful for example for improving the quality of a sward by preferential suppression of the growth of undesirable species.

The dwarfing may also be useful in miniaturising ornamental, household, garden and nursery plants (eg. poinsettias, chrysanthemums, carnations, tulips and daffodils).

As indicated above, the compounds can also be used to stunt woody species. This property can be used to control hedgerows or to shape or reduce the need for pruning, of fruit trees (eg. apples, pears, cherries, peaches, vines etc). Some coniferous trees are not significantly stunted by the compounds so the compounds could be useful in controlling undesirable vegetation in conifer nurseries.

The plant growth regulating effect may (as implied above) manifest itself in an increase in crop yield; or in an ability in orchards and other crops to increase fruit set, pod set and grain set.

In the potato, vine control in the field and inhibition of sprouting in the store may be possible.

Other plant growth regulating effects caused by the compounds include alteration of leaf angle and changes in leaf morphology (both of which may permit increased light interception and utilization) and promotion of tillering in monocotyledonous plants. Improved light interception is of value in all major world crops, eg. wheat, barley, rice, maize, soya, sugarbeet, potatoes, plantation crops and orchard crops. The leaf angle effect may be useful for example in altering the leaf orientation of, for example, potato crops thereby letting more light into the crops and inducing an increase in photosynthesis and tuber weight. By increasing tillering in monocotyledonous crops (eg. rice), the number of flowering shoots per unit area may be increased thereby increasing the overall grain yield of such crops. In addition better control and modification of hierarchical relationships is possible both in vegetative and reproductive stages of monocotyledonous and dicotyledenous plant growth, especially in cereals such as wheat, barley, rice and maize, whereby the number of flowering shoots per unit area may be increased and the size distribution of grains within the ear may be modified in such a way as to increase yield. In the treatment of rice plants, or rice crops the invention compounds can be applied, eg. as granules or a granular formulation, for example as slow release granules, to nursery boxes, paddy water and other like cultivation loci and media. In grass swards, especially amenity grass, an increase in tillering could lead to a denser sward which may result in increased resilience in wear; and to increased yields and better quality of forage grass, eg. improved digestability and palatability.

The treatment of plants with the compounds can lead to the leaves developing a darker green colour. In dicotyledonous plants such as soyabean and cotton, there may be promotion of sideshooting.

The compounds may inhibit, or at least delay, the flowering of sugar beet (and thereby may increase sugar yield) or otherwise modify the flowering patterns in many other crops. They may also reduce the size of sugar beet without reducing significantly the sugar yield thereby enabling an increase in planting density to be made. Similarly in other root crops (eg. turnip, swede, mangold, parsnip, beetroot, yam and cassava) it may be possible to increase the planting density.

The compounds could be useful in restricting the vegetative growth of cotton thereby leading to an increase in cotton yield. Crop yields may also be increased by improvement of the harvest index (ie. the harvested yield as a proportion of the total dry matter produced) by altering dry matter partitioning. This applies to all the aforements root, pod cereal, tree, plantation and orchard crops.

The compounds may be useful in rendering plants resistant to stress since the compounds can delay the emergence of plants grown from seed, shorten stem height and delay flowering; these properties could be useful in preventing frost damage in countries where there is significant snow cover in the winter since then the treated plants would remain below snow cover during the cold weather. Further the compounds may cause drought or cold resistance in certain plants.

When applied as seed treatments at low rates the compounds can have a growth stimulating effect on plants.

In carrying out the plant growth regulating method of the invention, the amount of compound to be applied to regulate the growth of plants will depend upon a number of factors, for example the particular compound selected for use, and the identity of the plant species whose growth is to be regulated. However, in general an application rate of 0.1 to 15, preferably 0.1 to 5, kg per hectare is used. With the use of biodegradable polymeric slow release granules rates of 1 to 10 g per hectare are feasible; whilst electrodynamic spraying techniques may also deploy lower rates of application. However, on certain plants even application rates within these ranges may give undesired phytotoxic effects. Routine tests may be necessary to determine the best rate of application of a specific compound for any specific purpose for which it is suitable.

The compounds may be used as such for fungicidal or plant growth regulating purposes but are more conveniently formulated into compositions for such usage. The invention thus provides a fungicidal or plant growth regulating composition comprising a compound of general formula (I) as hereinbefore defined, or a salt, metal complex, ether or ester thereof; and, optionally, a carrier or diluent.

The invention also provides a method of combating fungi, which comprises applying to a plant, to seed of a plant, or to the locus of the plant or seed, a compound, or salt, metal complex, ether or ester thereof, as hereinbefore defined.

The invention also provides a method of regulating plant growth, which comprises applying to the plant, to seed of a plant or to the locus of a plant or seed, a compound, or salt, metal complex, ether or ester thereof, as hereinbefore defined.

The compounds, salts, metal complexes, ethers and esters can be applied in a number of ways, for example they can be applied, formulated or unformulated, directly to the foliage of a plant, or they can be applied also to bushes and trees, to seeds or to other medium in which plants, bushes or trees are growing or are to be planted, or they can be sprayed on, dusted on or applied as a cream or paste formulation, or they can be applied as a vapour; or as slow release granules. Application can be to any part of the plant, bush or tree, for example to the foliage, stems, branches or roots, or to soil surrounding the roots, or to the seed before it is planted; or to the soil generally, or to paddy water or to hydroponic culture systems. The invention compounds may also be injected into plants or trees and they may also be sprayed onto vegetation using electrodynamic spraying techniques.

The term "plant" as used herein includes seedlings, bushes and trees. Furthermore, the fungicidal method of the invention includes preventative, protectant, prophylactic and eradicant treatment.

The compounds are preferably used for agricultural and horticultural purposes in the form of a composition. The type of composition used in any instance will depend upon the particular purpose envisaged.

The compositions may be in the form of dusting powders or granules comprising the active ingredient and a solid diluent or carrier, for example fillers such as kaolin, bentonite, kieselguhr, dolomite, calcium carbonate, talc, powdered magnesia, Fuller's earth, gypsum, Hewitt's earth, diatomaceous earth and China clay. Such granules can be preformed granules suitable for application to the soil without further treatment. These granules can be made either by impregnating pellets of filler with the active ingredient or by pelleting a mixture of the active ingredient and powdered filler. Compositions for dressing seed, for example, may comprise an agent (for example a mineral oil) for assisting the adhesion of the composition to the seed; alternatively the active ingredient can be formulated for seed dressing purposes using an organic solvent (for example N-methylpyrrolidone or dimethylformamide).

The compositions may also be in the form of dispersible powders, granules or grains comprising a wetting agent to facilitate the dispersion in liquids of the powder or grains which may contain also fillers and suspending agents.

The aqueous dispersions or emulsions may be prepared by dissolving the active ingredient(s) in an organic solvent optionally containing wetting, dispersing or emulsifying agent(s) and then adding the mixture to water which may also contain wetting, dispersing or emulsifying agent(s). Suitable organic solvents are ethylene dichloride, isopropyl alcohol, propylene glycol, diacetone alcohol, toluene, kerosene, methylnaphthalene, the xylenes, trichloroethylene, furfuryl alcohol, tetrahydrofurfuryl alcohol, and glycol ethers (eg. 2-ethoxyethanol and 2-butoxyethanol).

The compositions to be used as sprays may also be in the form of aerosols wherein the formulation is held in a container under pressure in the presence of a propellant, eg. fluorotrichloromethane or dichlorodifluoromethane.

The compounds can be mixed in the dry state with a pyrotechnic mixture to form a composition suitable for generating in enclosed spaces a smoke containing the compounds.

Alternatively, the compounds may be used in a micro-encapsulated form. They may also be formulated in biodegradable polymeric formulations to obtain a slow, controlled release of the active substance.

By including suitable additives, for example additives for improving the distribution, adhesive power and resistance to rain on treated surfaces, the different compositions can be better adapted for various utilities.

The compounds can be used as mixtures with fertilisers (eg. nitrogen-, potassium- or phosphorus-containing fertilisers). Compositions comprising only granules of fertiliser incorporating, for example coated with, the compound are preferred. Such granules suitably contain up to 25% by weight of the compound. The invention therefore also provides a fertiliser composition comprising the compound of general formula (I) or a salt or metal complex thereof.

The compositions may also be in the form of liquid preparations for use as dips or sprays which are generally aqueous dispersions or emulsions containing the active ingredient in the presence of one or more surfactants eg. wetting agent(s), dispersing agent(s), emulsifying agent(s) or suspending agent(s); or which are spray formulations of the kind suitable for use in electrodynamic spraying techniques. The foregoing agents can be cationic, anionic or non-ionic agents. Suitable cationic agents are quaternary ammonium compounds, for example cetyltrimethyl-ammonium bromide.

Suitable anionic agents are soaps, salts of aliphatic monoesters of sulphuric acid (for example sodium lauryl sulphate), and salts of sulphonated aromatic compounds (for example sodium dodecylbenzenesulphonate, sodium, calcium or ammonium lignosulphonate, butylnaphthalene sulphonate, and a mixture of sodium diisopropyl- and triisopropylnaphthalene sulphonates).

Suitable non-ionic agents are the condensation products of ethylene oxide with fatty alcohols such as oleyl or cetyl alcohol, or with alkyl phenols such as octyl- or nonyl-phenol and octylcresol. Other non-ionic agents are the partial esters derived from long chain fatty acids and hexitol anhydrides, the condensation products of the said partial esters with ethylene oxide, and the lecithins. Suitable suspending agents are hydrophilic colloids (for example polyvinylpyrrolidone and sodium carboxymethylcellulose), and the vegetable gums (for example gum acacia and gum tragacanth).

The compositions for use as aqueous dispersions or emulsions are generally supplied in the form of a concentrate containing a high proportion of the active ingredient(s), and the concentrate is to be diluted with water before use. These concentrates often should be able to withstand storage for prolonged periods and after such storage be capable of dilution with water in order to form aqueous preparations which remain homogeneous for a sufficient time to enable them to be applied by conventional and electrodynamic spray equipment. The concentrates may conveniently contain up to 95%, suitably 10-85%, for example 25-60%, by weight of the active ingredient(s). These concentrates suitably contain organic acids (eg. alkaryl or aryl sulphonic acids such as xylenesulphonic acid or dodecyl benzenesulphonic acid) since the presence of such acids can increase the solubility of the active ingredient(s) in the polar solvents often used in the concentrates. The concentrates suitably contain also a high proportion of surfactants so that sufficiently stable emulsions in water can be obtained. After dilution to form aqueous preparations, such preparations may contain varying amounts of the active ingredient(s) depending upon the intended purpose, but an aqueous preparation containing 0.0005% or 0.01% to 10% by weight of active ingredient(s) may be used.

The compositions of this invention can comprise also other compound(s) having biological activity, eg. compounds having similar or complementary fungicidal or plant growth activity or compounds having plant growth regulating, herbicidal or insecticidal activity.

The other fungicidal compound can be, for example, one which is capable of combating ear diseases of cereals (eg. wheat) such as Septoria, Gibberella and Helminthosporium spp., seed and soil borne diseases and downy and powdery mildews on grapes and powdery mildew and scab on apple etc. These mixtures of fungicides can have a broader spectrum of activity than the compound of general formula (I) alone; further the other fungicide can have a synergistic effect on the fungicidal activity of the compound of general formula (I). Examples of the other fungicidal compound are imazalil, benomyl, carbendazim, thiophanate-methyl, captafol, captan, sulphur, triforine, dodemorph, tridemorph, pyrazophos, furalaxyl, ethirimol, tecnazene, dimethirimol, bupirimate, chlorothalonil, vinclozolin, procymidone, iprodione, metalaxyl, forsetyl-aluminium, carboxin, oxycarboxin, fenarimol, nuarimol, fenfuram, methfuroxan, nitrotal-isopropyl, triadimefon, thiabendazole, etridiazole, triadimenol, biloxazol, dithianon, binapacryl, quinomethionate, guazatine, dodine, fentin acetate, fentin hydroxide, dinocap, folpet, dichlofluanid, ditalimphos, kitazin, cycloheximide, dichlobutrazol, a dithiocarbamate, a copper compound, a mercury compound, 1-(2-cyano-2-methoxyiminoacetyl)-3-ethyl urea, fenapanil, ofurace, propiconazole, etaconazole and fenpropemorph.

The compounds of general formula (I) can be mixed with soil, peat or other rooting media for the protection of plants against seed-borne, soil-borne or foliar fungal diseases.

Suitable insecticides are Pirimor, Croneton, dimethoate, Metasystox and formothion.

The other plant growth regulating compound can be one which controls weeds or seedhead formation, improves the level or longevity of the plant growth regulating activity of the compounds of general formula (I), selectively controls the growth of the less desirable plants (eg. grasses) or causes the compound of general formula (I) to act faster or slower as a plant growth regulating agent. Some of these other agents will be herbicides.

Examples of suitable plant growth regulating compounds, which can display synergy in admixture, or use, with the invention compounds are the gibberellins (eg. $GA_3$, $GA_4$ or $GA_7$), the auxins (eg. indoleacetic acid, indolebutyric acid, naphthoxyacetic acid or naphthylacetic acid), the cytokinins (eg. kinetin, diphenylurea, benzimidazole, benzyladenine or benzylaminopurine), phenoxyacetic acids (eg. 2,4-D or MCPA), substituted benzoic acids (eg. triiodobenzoic acid), morphactins (eg. chlorfluorecol), maleic hydrazide, glyphosate, glyphosine, long chain fatty alcohols and acids, dikegulac, fluoridamid, mefluidide, substituted quaternary ammonium and phosphonium compounds (eg. chlormequat* chlorphonium or mepiquatchloride), ethephon, carbetamide, methyl-3,6-dichloroanisate, daminozide*, asulam, abscisic acid, isopyrimol, 1-(4-chlorophenyl)-4,6-dimethyl-2-oxo-1,2-dihydropyridine-3-carboxylic acid, hydroxybenzonitriles (eg. bromoxynil), difenzoquat, benzoylprop-ethyl 3,6-dichloropicolinic acid, and tecnazene. Synergy will be most likely to occur with those of the foregoing which are quaternary ammonium compounds in particular those marks with an asterisk.

The use of the compounds of general formula (I) in conjunction with gibberellins can be useful where it is desired to reduce the plant growth regulating effects of the compounds (eg. where they are to be used as fungicides). Where the compounds are being applied to the soil surrounding the plants or to the roots of the plant, the plant growth regulating effects of the compounds may possibly be reduced by using also certain types of phenoxybenzoic acids and their derivatives.

The following Examples illustrate the invention; the temperatures are given in degrees Centrigrade (°C.).

EXAMPLE 1

This Example illustrates the preparation of a compound having the structure:

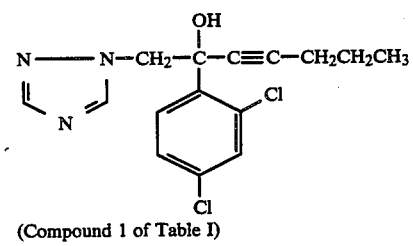

(Compound 1 of Table I)

1,2,4-Triazole (1.89 g) was added portionwise to a stirred suspension of sodium hydride (1.32 g, 50% dispersion in oil) in dry DMF (75 ml). When reaction was complete the chlorohydrin (4.0 g), prepared as described below, in dry DMF (10 ml) was added dropwise to the stirred solution, which was then heated to 80°-90° for 3-4 hours (when all the starting material was disappeared on GLC). The mixture was cooled and poured into water and extracted three times with ether. The ethereal extracts were washed with water, dried over magnesium sulphate and evaporated. This yielded a gum which crystallised to a cream powder (2.5 g) mpt 83°–5°.

NMR (CDCl$_3$) δ0.90 (t, 3H) 1.46 (sextet, 2H), 2.13 (t, 2H), 4.72 (d, 1H), 4.88 (d, 1H), 5.90 (bs, OH), 7.22 (dd, 1H), 7.46 (d, 1H), 7.75 (d, 1H), 7.84 (s, 1H), 8.20 (s, 1H).

IR (nujol) 3200, 2230 (weak) cm$^{-1}$.

The chlorohydrin used in the foregoing reaction, and of formula

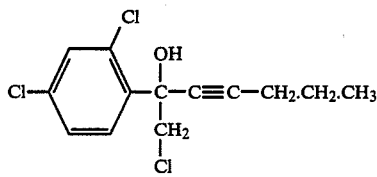

was prepared as follows:

n-Butyl lithium (18.75 ml of a 1.6 m solution in hexane) was added dropwise to a stirred, cooled solution of 1-pentyne (3.0 ml in dry THF, 20 ml) at −78° C., under argon. After completion of the addition the clear solution was stirred at −78° for 15 minutes. 2,2′,4′-trichloroacetophenone (5.0 g) in dry THF (20 ml) was added dropwise, keeping the temperature below −68° C. During the addition the reaction was monitored by GLC, and addition of the acetophenone stopped when it was no longer consumed. After stirring for a further 30 minutes, the reaction was poured into water and extracted with ether. The ether extract was washed with water, dried and evaporated to give a yellow liquid (5.5 g). The compound was pure by NMR and GLC.

NMR (CDCl$_3$) δ1.0 (t, 3H), 1.55 (sextet, 2H) 2.24 (t, 2H) 3.56 (s, OH), 3.95 (d, 2H), 4.19 (d, 2H), 7.30 (dd, 1H), 7.40 (d, 1H) 7.86 (d, 1H)

IR (liquid film) 3300 (strong), 2230 (weak) cm$^{-1}$.

EXAMPLE 2

This Example illustrates the preparation of Compound No 4 of Table I having the formula:

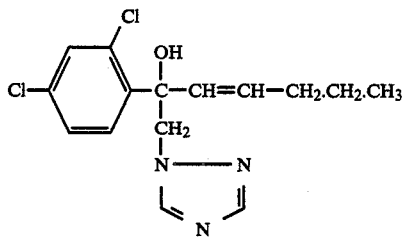

Trans isomer

Lithium aluminium hydride (51 mg) was added portionwise to a stirred solution of the pentynyl triazole prepared in Example 1 in dry ether (20 ml). When addition was complete the mixture was heated to reflux and was monitored by GLC. After a total of 56 hours reflux and addition of a further 100 mg of LiAlH$_4$, all the starting material had gone. The reaction was cooled and poured very carefully into 100 ml of water and 15 ml dilute hydrochloric acid, and extracted with ether. The ethereal extracts were washed with water, dried and evaporated. The residue was flash chromatographed on silica gel eluting with methylene chloride/methanol 98:2. The product was isolated as a clear oil which crystallised on scratching with ether/petrol. The white powder obtained (200 mg) had mpt 94°–5° C.

NMR (CDCl$_3$) δ0.86 (t, 3H), 1.38 (sextet, 2H), 2.03 (q, 2H), 4.70 (d, 1H), 5.60–6.0 (m, 1H), 6.10 (d, 1H), 7.25 (dd, 1H), 7.45 (d, 1H), 7.78 (d, 1H), 7.88 (s, 1H), 8.13 (s, 1H).

EXAMPLE 3

By methods similar to those described in Examples 1 and 2 the following compounds were prepared having the physical characteristics recited.

Compound No 2 of Table 1

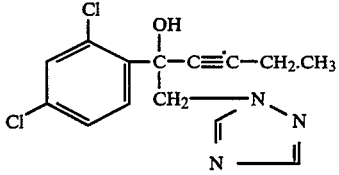

NMR (CDCl$_3$) 1.05 (t, 3H), 2.18 (q, 2H), 4.72 (d, 1H), 4.90 (d, 1H), 5.30 (s, OH), 7.30 (dd, 1H), 7.52 (d, 1H), 7.84 (d, 1H), 7.95 (s, 1H), 8.25 (s, 1H).

IR (nujol) 3200, 2240 (weak) cm$^{-1}$.

mpt 129°–30° (white solid).

Compound No 4 of Table 1

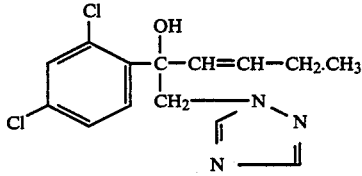

Trans isomer

NMR (CDCl$_3$) 0.92 (t, 3H), 2.05 (quintet, 2H), 4.64 (d, 1H) 5.00 (s, OH), 5.06 (d, 1H), 5.60–6.04 (m, 1H), 6.02 (d, 1H), 7.14 (dd, 1H), 7.34 (d, 1H), 7.68 (d, 1H), 7.76 (s, 1H), 8.00 (s, 1H)

IR (nujol) 3110 cm$^{-1}$.

mpt 109°–110° (chunky white crystals).

Compound No 14 of Table 1

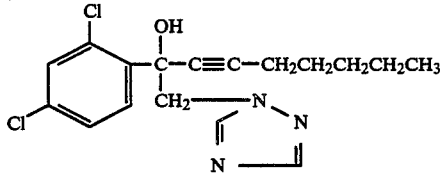

NMR (CDCl$_3$) 0.84 (t, 3H), 1.10–1.60 (m, 4H), 2.14 (t, 2H), 4.74 (d, 1H), 4.92 (d, 1H), 5.80 (s, OH), 7.30 (dd, 1H), 7.86 (d, 1H), 7.96 (s, 1H), 8.32 (s, 1H).

IR (nujol) 3070, 2230 (weak) cm$^{-1}$.

mpt 83°–4° C. (white crystals).

Compound No 15 of Table 1

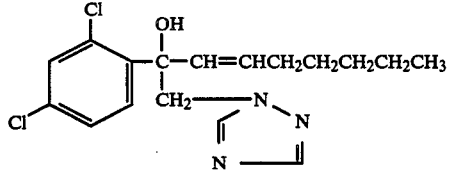

Trans isomer

NMR (CDCl$_3$) 0.87 (t, 3H), 1.05–1.50 (m, 4H), 1.90–2.20 (m, 2H), 4.62 (d, 1H), 4.70 (s, OH), 5.06 (d, 1H), 5.54–6.0 (m, 1H), 6.02 (d, 1H), 7.15 (dd, 1H), 7.6 (d, 1H), 7.68 (d, 1H), 7.80 (s, 1H) 8.0 (s, 1H).

IR (nujol) 3070 cm$^{-1}$.

mpt 58°–61° (white powdery crystals).

EXAMPLE 4

This example illustrates the preparation of the compounds having the chemical formula:

(Compound No. 5 of Table 1)

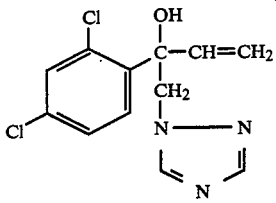

STAGE 1

Vinylmagnesium bromide (formed from 1.6 g of magnesium turnings and 3.74 g of vinyl bromide in 35 ml of dry THF) was added dropwise by syringe to a stirred solution of 2,4-dichlorophenacyl chloride (5.5 g) in dry ether (35 ml) under argon. The rate of addition was adjusted so that a gentle reflux was obtained. Thirty minutes after completion of the addition the reaction was cooled and was poured into saturated ammonium chloride. The aqueous layer was extracted twice with ether, the organic extracts combined, dried and evaporated to yield an oil (4.4 g). NMR analysis showed the presence of the chlorohydrin of formula:

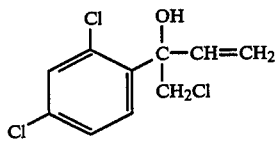

and a little starting material. The material was used without further purification.

NMR (CDCl$_3$) 2.96 (d, 1H), 3.12 (d, 1H), 4.90–5.30 (m, 2H), 5.60–5.90 (m, 1H), 7.10–7.60 (m, 4H).

IR (liquid film) 3350 (bs).

STAGE 2

The preparation of the compound having the formula:

(Compound No 5 of Table 1)

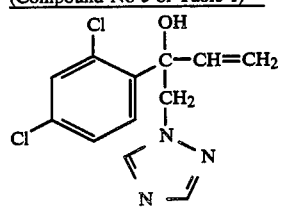

1,2,4-Triazole (2,6 g) in dry DMF (5 ml) was added dropwise to a stirred suspension of sodium hydride (1.8 g of a 50% dispersions in oil with the oil washed off prior to use) in dry DMF (15 ml). The temperature rose to 40° C. The solution was stirred at room temperature for 30 minutes after completion of the addition. The chlorohydrin from the previous reaction (4.4 g) in dry DMF (5 ml) was added all at once and the mixture was heated to 50° C. for 5 hours and then stood overnight at room temperature. The mixture was poured into water and then extracted three times with ether. The ether extracts were washed with water, dried and evaporated to give a dark oil (4.0 g). The oil was flash chromatographed, eluting with ethyl acetate, and the desired product was isolated as a brown oil which crystallised on scratching with ether/petroleum, yielding 0.55 g, mpt. 88°–90° C.

NMR (CDCl$_3$) 4.75–5.70 (m, 5H), 3.70 (dd, 1H), 7.44 (dd, 1H), 7.60 (d, 1H), 7.95 (d, 1H), 8.08 (s, 1H), 8.28 (s, 1H).

IR (nujol) $\nu$ 3120 cm$^{-1}$(s).

EXAMPLE 5

This Example illustrates the preparation of compound No 6 of Table I.

STAGE 1

The preparation of the epoxide having the formula:

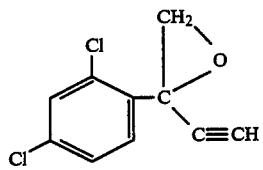

Acetylene gas, scrupulously dried, was bubbled into dry THF (25 ml) at −78° C., until 1g had been dissolved. Argon was then introduced, and n-butyl lithium (15.4 ml of a 1.6 m solution in hexane) was then added dropwise, keeping the temperature below −69° C. On completion of the addition 2,4-dichlorophenacyl chloride (5.0 g) in dry THF (10 ml) was slowly added keeping the temperature at −70° C. to −75° C. After completion of the addition the mixture was stirred for 30 minutes and then warmed to room temperature overnight. The brown solution was poured into aqueous ammonium chloride. The organic layer was separated and dried and evaporated to give a brown oil, which was distilled (90° C./0.03 mm). The liquid crystallised to a solid (2.4 g, mpt 40°–44° C.).

NMR (CDCl$_3$) 2.62(s, 1H), 4.70(d, 1H), 4.96(d, 1H), 6.16(s, 1H), 7.32(dd, 1H), 7.48 (d, 1H), 7.96(d, 1H), 7.95(s, 1H), 8.20(s, 1H).

IR (nujol)$\nu$3265 cm$^{-1}$, 3120 cm$^{-1}$ (w).

STAGE 2

The preparation of the compound having formula:

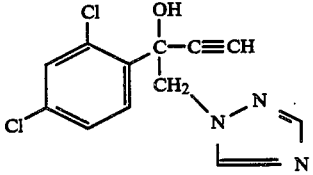

1,2,4-Triazole (0.48 g) was added in dry DMF (5 ml) dropwise to sodium hydride (0.34 g of a 50% dispersion in oil) in dry DMF (15 ml) to form the anion. After completion of the addition the mixture was stirred at room temperature for 30 minutes. The epoxide from the previous reaction (1.0 g) in dry DMF (15 ml) was slowly added dropwise and then the mixture heated to 50° C. for 4 hours. After standing at room temperature overnight the solution was poured into water and extracted with ether. The extract was dried and evaporated to give a brown oil, which was purified by flash chromatography, eluting with ethyl acetate to give a brown oil which crystallised on scratching with ether, to give a pale brown powder mpt 129°-131° (0.52 gm).

NMR (CDCl$_3$) 2.36 (s, 1H), 2.70(d, 1H), 3.36(d, 1H), 7.10–7.50(m, 3H).

IR(liquid film) 3300 cm$^{-1}$ (s), 2120 cm$^{-1}$ (w).

EXAMPLE 6

An emulsifiable concentrate was made up by mixing the ingredients, and stirring the mixture until all the constituents were dissolved.

| | |
|---|---|
| Compound of Example 1 | 10% |
| Ethylene dichloride | 40% |
| Calcium dodecylbenzenesulphate | 5% |
| "Lubrol" L | 10% |
| "Aromasol" H | 35% |

EXAMPLE 7

A composition in the form of grains readily dispersible in a liquid, e.g. water, was prepared by grinding together the first three ingredients in the presence of added water and then mixing in the sodium acetate. The resultant mixture was dried and passed through a British Standard mesh sieve, size 44-100, to obtain the desired size of grains.

| | |
|---|---|
| Compound of Example 2 | 50% |
| "Dispersol" T | 25% |
| "Lubrol" APN5 | 1.5% |
| Sodium acetate | 23.5% |

EXAMPLE 8

The ingredients were all ground together to produce a powder formulation readily dispersible in liquids.

| | |
|---|---|
| Compound of Example 3 | 45% |
| "Dispersol" T | 5% |
| "Lissapol" NX | 0.5% |
| "Cellofas" B600 | 2% |
| Sodium acetate | 47.5% |

EXAMPLE 9

The active ingredient was dissolved in a solvent and the resultant liquid was sprayed on to the granules of China clay. The solvent was then allowed to evaporate to produce a granular composition.

| | |
|---|---|
| Compound of Example 4 | 5% |
| China clay granules | 95% |

EXAMPLE 10

A composition suitable for use as a seed dressing was prepared by mixing the three ingredients.

| | |
|---|---|
| Compound of Example 1 | 50% |
| Mineral oil | 2% |
| China clay | 48% |

EXAMPLE 11

A dusting powder was prepared by mixing the active ingredient with talc.

| | |
|---|---|
| Compound of Example 2 | 5% |
| Talc | 95% |

EXAMPLE 12

A Col formulation was prepared by ball-milling the constituents set out below and then forming an aqueous suspension of the ground mixture with water.

| | |
|---|---|
| Compound of Example 3 | 40% |
| "Dispersol" T | 10% |
| "Lubrol" APN5 | 1% |
| Water | |

EXAMPLE 13

A dispersible powder formulation was made by mixing together the ingredients set out below and then grinding the mixture until all were thoroughly mixed.

| | |
|---|---|
| Compound of Example 4 | 25% |
| "Aerosol" OT/B | 2% |
| "Dispersol" A.C. | 5% |
| China clay | 28% |
| Silica | 40% |

EXAMPLE 14

This Example illustrates the preparation of a dispersible powder formulation. The ingredients were mixed and the mixture then ground in a comminution mill.

| | |
|---|---|
| Compound of Example 1 | 25% |
| "Perminal" BX | 1% |
| "Dispersol" T | 5% |
| Polyvinylpyrrolidone | 10% |
| Silica | 25% |
| China clay | 34% |

EXAMPLE 15

The ingredients set out below were formulated into a dispersible powder by mixing then grinding the ingredients.

| | |
|---|---|
| Compound of Example 2 | 25% |
| "Aerosol" OT/B | 2% |
| "Dispersol" A | 5% |
| China clay | 68% |

In Examples 5 to 14 the proportions of the ingredients given are by weight.

All the compounds of Table I were formulated in the same way as set out in Examples 6 to 15.

There now follows an explanation of the compositions or substances represented by the various Trade Marks and Trade Names mentioned above.

| | |
|---|---|
| LUBROL L: | a condensate of nonyl phenol (1 mole) with ethylene oxide (13 moles) |
| AROMASOL H: | a solvent mixture of alkylbenzenes |
| DISPERSOL T & AC: | a mixture of sodium sulphate and a condensate of formaldehyde with sodium naphthalene sulphonate |

EXAMPLE 16

The compounds were tested against a variety of foliar fungal diseases of plants. The technique employed was as follows.

The plants were grown in John Innes Potting Compost (No 1 or 2) in 4 cm diameter minipots. A layer of fine sand was placed at the bottom of the pots containing the dicotyledonous plants to facilitate uptake of test compound by the roots.

The test compounds were formulated either by bead milling with aqueous Dispersol T or as a solution in acetone or acetone/ethanol which was diluted to the required concentration immediately before use. For the foliage diseases, suspensions (100 ppm active ingredient) were sprayed on to the soil. Exceptions to this were the tests on *Botrytis cinerea, Plasmopara viticola* and *Venturia inaequalis*. The sprays were applied to maximum retention and the root drenches to a final concentration equivalent to approximately 40 ppm a.i./dry soil. Tween 20, to give a final concentration of 0.05%, was added when the sprays were applied to cereals.

For most of the tests the compound was applied to the soil (roots) and to the foliage (by spraying) one or two days before the plant was inoculated with the diseases. An exception was the test on *Erysiphe graminis* in which the plants were inoculated 24 hours before treatment. After inoculation, the plants were put into an appropriate environment to allow infection to take place and then incubated until the disease was ready for assessment. The period between inoculation and assessment varied from four to fourteen days according to the disease and environment.

The disease control was recorded by the following grading:
4 = no disease
3 = trace-5% of disease on untreated plants
2 = 6-25% of disease on untreated plants
1 = 26-59% of disease on untreated plants
0 = 60-100% of disease on untreated plants The results are shown in Table II.

TABLE II

| COMPOUND NUMBER | PUCCINIA RECONDITA (WHEAT) | ERYSIPHE GRAMINIS (BARLEY) | PIRICULARIA ORYZAE (RICE) | PLASMOPARA VITICOLA (VINE) | PHYTOPHTHORA INFESTANS (TOMATO) | BOTRYTIS CINEREA (GRAPE OR TOMATO) | CERCOSPORA ARACHIDICOLA (PEANUT) | VENTURIA INAEQUALIS (APPLE) |
|---|---|---|---|---|---|---|---|---|
| 1 | 4 | 4 | 3 | 0 | — | 0 | 4 | 4 |
| 2 | 4 | 4 | 4 | 1 | — | 4 | 4 | 4 |
| 3 | 4 | 4 | 3 | 3 | — | 4 | 4 | — |
| 4 | 4 | 4 | 4 | 1 | — | 2 | 4 | 4 |
| 5 | 4 | 4 | — | 0 | — | 0 | 4 | 4 |
| 6 | 4 | 4 | — | 0 | — | 0 | 4 | 4 |
| 7 | 4 | 4 | 4 | 1 | — | — | — | 4 |
| 8 | 4 | 4 | 3 | 0 | — | — | — | 4 |
| 9 | 4 | 4 | 4 | 0 | — | — | 4 | 4 |
| 13 | 4 | 4 | 2 | 0 | — | — | — | 4 |

EXAMPLE 17

This Example illustrates the plant growth regulating properties of the compounds. The compounds were applied as an overall spray of an emulsifiable concentrate diluted to give the concentrations shown in Table III. The plants were grown in 3" pots in peat compost and sprayed at the 2 leaf stage. Pleant growth regulating effects were assessed 13 or 19 days after application of the compounds. Retardation of growth was scored on a 1-3 scale where:
1 = 0-30% retardation
2 = 31-75% retardation
3 = 75% retardation or more
The absence of any numeral 1 to 3 signifies no effect.

Additional plant growth regulating properties are indicated as follows:
G = darker green leaf colour
A = apical effect
T = tillering effect The results are shown in Table III. If no figure is shown the compounds was substantially inactive as a stunting agent.

TABLE III

| COMPOUND | DAT | RATE (ppm) | AT | CC | DA | LT | SB | TO | SY | CT | MZ | WW | BR |
|---|---|---|---|---|---|---|---|---|---|---|---|---|---|
| 1 | 13 | 4000 | — | — | — | 2GH | 2GA | 2GTA | 2G | 3GA | 2G | 1G | — |
| 2 | 12 | 4000 | 1 | 1 | 1 | 3G | 3GA | 2G | 2G | 2GA | 2G | 1T | 1T |
| 14 | 12 | 4000 | — | — | — | 2G | 3G | 2GA | 2G | — | 1 | 1 | — |
| 4 | 12 | 4000 | 2 | 2G | 2G | 3G | 3GA | 3GA | 2G | 3GA | 3GA | 1G | 2G |
| 15 | 12 | 3500 | 2G | 1G | 1G | 3GA | 3GA | 3GA | 3G | 3G | 1 | 1T | 2 |
| 5 | 19 | 4000 | 2G | 1 | 1 | 3H | 3G | 2G | 3QT | — | 3G | 2G | 1 |
| 6 | 19 | 4000 | — | — | 2 | 1G | 3G | 2GT | 2GT | 3GAT | 2 | 1 | 1 |
| 9 | 19 | 4000 | — | 1 | 1 | — | 2G | 2G | 1G | * | 1G | T | T |

TABLE III-continued

| COMPOUND | DAT | RATE (ppm) | AT | CC | DA | LT | SB | TO | SY | CT | MZ | WW | BR |
|---|---|---|---|---|---|---|---|---|---|---|---|---|---|
| 7 | 19 | 4000 | 1 | 1 | 1 | 2 | 3G | 3G | 1G | * | 1G | 1T | 2T |

AT *Agrostis tenuis*
CC *Cynosurus cristatus*
DA *Dactylis glomerata*
LT *Lactuca sativa*
SB *Beta vulgaris*
TO *Lycopersicum esculentum*
SY *Glycine max*
CT *Gossypium hirsutum*
MZ *Zea mays*
WW *Triticum aestivum*
BR *Hordeum vulgare*

EXAMPLE 18

The compounds were tested against a range of foliar diseases of plants. The techniques employed were as follows.

For all tests, the plants were grown in John Innes Potting Compost (No. 1 or 2) in 4 cm diameter minipots. A layer of fine sand was placed at the bottom of the pots containing the dicotyledonous plants to facilitate uptake of test compounds by the roots. The test compounds were formulated either by bead milling with aqueous Dispersol T or as a solution in acetone or acetone/ethanol which was diluted to the required concentration immediately before use.

For all diseases, solutions and suspensions were either sprayed on the foliage to maximum retention or applied to the roots of the plant via the soil ("syst"). Tween 20, to give a final concentration of 0.05%, was added when the sprays were applied to cereals.

Foliar applications were eradicant ("erad") where the compound was applied one day after inoculation, and protectant ("prot"), where the chemical was applied one or two days before the plant was inoculated with the pathogen. Inoculation was achieved by spraying spore suspensions onto the leaves of the test plants. The plants were then placed in an appropriate environment to allow infection to proceed and the incubated until the disease was ready for assessment. The period between inoculation and assessment varied from four to fourteen days according to the disease and the environment.

Disease control was recorded using the following grading system:
4=no disease
3=trace to 5% of disease on untreated plants
2=6-25% of disease on untreated plants
1=26-59% of disease on untreated plants
0=60-100% of disease on untreated plants The results presented in Table IV are the lowest concentrations (in ppm) at which chemicals allowed greater than 5% disease to develop (ie. the dose range at which control passes from grade 3 to 2) in the *Cercospora arachidicola*, *Podosphaera leucotricha*, *Venturia inaequalis* and *Uncinula necator* tests. For the tests with *Erysiphe graminis* and *Puccinia recondita* the results are the lowest concentrations at which chemicals allowed greater than 25% disease to develop (ie. the dose range at which control passes from 2 to 1). Protectant ("prot"), eradicant ("erad") and systemic ("syst") results are given in the table.

It should be noted that in the table the presentation style, for example:

| 0.01–0.05 |
|---| signifies that the concentration in parts per million (ppm) lay between the values of 0.01 ppm and 0.05 ppm in the particular instance in question. The sign "<" indicates "below" or "less than" and ">" means "above" or "greater than" the particular concentration figure given.

The results demonstrate that in the vast majority of comparisons, compounds 1 to 6 of Table I are more active than compounds 1 to 55 of Table I of European Patent Application No. 81304835.2. Compounds 1–6 are not only more active against specific diseases but their overall distribution of protectant, eradicant and systemic properties across spectrum of target renders them more useful as broad-spectrum agricultural fungicides.

TABLE IV

| Compound No. | Egt Prot | Egt Syst | Pr Prot | Pr Syst | Pl Erad | Pl Prot | Pl Syst | Vi Erad | Vi Prot | Vi Syst | Un Erad | Un Prot | Un Syst | Ca Prot | Ca Syst |
|---|---|---|---|---|---|---|---|---|---|---|---|---|---|---|---|
| 1 | 0.01–0.05 | 0.1–0.5 | <0.1 | 0.1–0.5 | 1.0–2.5 | 1.0–2.5 | 1.0–2.5 | 0.5–1.0 | 2.5–10 | >10 | 0.05–0.25 | 0.01–0.05 | >2.5 | 1.0–5.0 | >5.0 |
| 2 | <0.05 | <0.05 | 0.1–0.5 | <0.1 | 0.1–0.25 | 1.0–2.5 | 0.1–0.25 | 0.25–0.5 | 1.0–2.5 | 1.0–2.5 | <0.05 | 0.05–0.25 | 0.1–0.25 | 0.25–1.0 | 1.0–5.0 |
| 3 | 0.05–0.1 | 0.5–1.0 | <0.1 | 1.0–5.0 | 0.25–1.0 | | >5.0 | 0.5–1.0 | >2.5 | >2.5 | | | | 0.25–1.0 | >10 |
| 4 | <0.01 | 0.1–0.5 | <0.1 | 0.1–0.5 | 1.0–5.0 | 1.0–5.0 | 1.0–5.0 | 0.5–1.0 | 1.0–2.5 | 1.0–2.5 | <0.25 | 0.05–0.25 | 0.25–1.0 | 1.0–5.0 | >5.0 |
| 5 | <0.01 | 0.01–0.05 | >1.0 | 0.5–5.0 | 1.0–5.0 | 1.0–5.0 | 1.0–5.0 | 2.5–10 | 2.5–10 | 0.5–2.5 | <0.25 | 0.25–1.0 | <0.25 | <0.5 | 0.5–2.5 |
| 6 | <0.1 | 0.1–0.5 | >5.0 | 1.0–5.0 | 5–10 | >10 | >10 | | >100 | | 0.5–1.0 | 1.0–5.0 | | >100 | >10 |
| 1' | <0.5 | >5 | 5–10 | 10 | 0.25–1.0 | >10 | >10 | 1.0–5.0 | 10–25 | 25 | 0.05 | 0.01–0.05 | 2.5–5.0 | 1.0–5.0 | >10 |
| 2' | <0.1 | 0.1–0.5 | <0.5 | 0.5–1.0 | >10 | >10 | | | >25 | >25 | 1.0–5.0 | 1.0–5.0 | >10 | >25 | >25 |
| 3' | <0.5 | <0.5 | >10 | 10–25 | >10 | >10 | | | >25 | >25 | | | | >25 | >25 |
| 4' | 0.5–1.0 | >5.0 | >25 | >25 | | >10 | | | >25 | >25 | | | | *>100 | >25 |
| 5' | >5.0 | | >25 | >25 | | | | | *>100 | | 2.5–5.0 | 5.0–10 | | 5.0–10 | 5.0–10 |
| 6' | 1.0–5.0 | 1.0–5.0 | 10–25 | 5.0–10 | 0.1–2.5 | 2.5–5.0 | 2.5–5.0 | >10 | 10–25 | 5–10 | >10 | 1.0–2.5 | 1.0–2.5 | >100 | |
| 7 | <0.5 | <0.5 | 10–25 | <1.0 | >10 | >10 | >10 | *>100 | *>100 | | <5 | <10 | | >25 | 10–25 |
| 8 | | >5 | >10 | >10 | | | | | | | | | | | >25 |
| 9 | >1.0 | >10 | >5.0 | >5.0 | 1.0–2.5 | 1.0–5.0 | >10 | >10 | 10–25 | >10 | 0.5–1.0 | 1.0–2.5 | >10 | 10–25 | ≦10 |
| 10 | <0.1 | 0.1–0.5 | >5.0 | >5.0 | >10 | >5.0 | >10 | *>100 | *>100 | | 0.5–5.0 | 0.5–5.0 | >10 | >25 | 10–25 |
| 11 | <0.1 | >1.0 | >5.0 | >5.0 | | | >5.0 | *>100 | *>100 | | | | >5.0 | 10–25 | >25 |
| 12 | >1.0 | 0.1–0.5 | 1.0–5.0 | 1.0–5.0 | 1.0–5.0 | 2.5–5.0 | | 10–25 | >25 | 10–25 | 1.0–5.0 | 1.0–5.0 | | >100 | ≦10 |
| 13 | 0.5–5.0 | 0.5–1.0 | >5.0 | >5.0 | 1.0–5.0 | 1.0–5.0 | | 2.5–5.0 | 10–25 | >25 | 1.0–5.0 | 0.1–0.25 | | 2.5–10 | 10–25 |
| 14 | 0.1–0.5 | >1.0 | 1.0–5.0 | >5.0 | 0.25–5.0 | | | 2.5–10 | 10–25 | 10–25 | 0.1–0.25 | | >10 | >25 | 10–25 |
| 15 | >1.0 | >1.0 | >5.0 | 1.0–5.0 | 5–10 | >10 | >10 | *>100 | *>100 | | | | | *>100 | |
| 16 | <0.5 | 0.5–1.0 | 1.0–5.0 | 0.5–1.0 | 0.25–1.0 | >10 | >10 | 10–25 | 10–25 | >25 | 0.05 | 0.01–0.05 | >5.0 | 2.5–10 | >10 |
| 17 | 0.1–0.5 | >1.0 | 5.0–25 | 10–25 | | >10 | >10 | >10 | >10 | >25 | 1.0–5.0 | 1.0–5.0 | >10 | <25 | >25 |
| 18 | <0.1 | >1.0 | >25 | >25 | | >5.0 | | | >25 | >25 | 0.25–1.0 | 0.25–1.0 | | >100 | >25 |
| 19 | 0.1–0.5 | >1.0 | >5.0 | >5.0 | >5.0 | >5.0 | >5.0 | | >25 | >100 | | | | >10 | >25 |
| 20 | <0.5 | >1.0 | >5.0 | >5.0 | >5.0 | >5.0 | >5.0 | | >25 | >25 | 0.25–1.0 | 0.25–1.0 | | *>100 | 2.5–10 |
| 21 | | | | 10–5.0 | 1.0–5.0 | >5.0 | 1.0–5.0 | | >25 | >25 | | | | >25 | >25 |
| 22 | <0.5 | <0.5 | >5.0 | >5.0 | | | >5.0 | | >25 | >25 | | | | >25 | >25 |
| 23 | >1.0 | 0.1–0.5 | 0.5–1.0 | >5.0 | | | 5.0 | | 2.5–<10 | >10 | | | >5.0 | 0.5–2.5 | >25 |
| 24 | <0.1 | <0.1 | 1.0–5.0 | >5.0 | | | | | 10–25 | >10 | <0.05 | | 0.25–1.0 | <25 | >25 |
| 25 | <0.1 | >1.0 | 1.0–5.0 | >5.0 | 0.25 | | | | >25 | >25 | | | 1.0–5.0 | >10 | >25 |
| 26 | 0.1–0.5 | 0.5–1.0 | 1.0–5.0 | >5.0 | | 1.0–5.0 | | | 2.5–10 | >10 | | | | *>100 | >25 |
| 27 | <0.1 | >1.0 | 1.0–5.0 | <0.5 | | | | | 10–25 | 10–25 | 1.0–5.0 | 1.0–5.0 | >5.0 | >25 | >25 |
| 28 | 0.1–0.5 | >1.0 | 1.0–5.0 | <0.5 | >5.0 | >5.0 | >5.0 | | 10–25 | 10–25 | ≦0.25 | 0.05–0.1 | 5.0 | 0.5–2.5 | 0.5–2.5 |
| 29 | 0.1–0.5 | >1.0 | 1.0–5.0 | >5.0 | 1.0–5.0 | >5.0 | >5.0 | 1.0–5.0 | 2.5–10 | 10–25 | 0.25–1.0 | 1.0–5.0 | >5.0 | 5.0–10 | 10–25 |
| 30 | | | | | >5.0 | >5.0 | | | 10–25 | 10–25 | 1.0–5.0 | 1.0–5.0 | | 10–25 | 10–25 |
| 31 | 0.1–0.5 | >1.0 | 1.0–5.0 | 1.0–5.0 | 0.25–1.0 | >5.0 | >5.0 | >10 | 10–25 | 10–25 | 0.1–0.25 | 0.1–0.25 | >5.0 | ≦10 | >10 |
| 32 | 0.5–1.0 | >1.0 | 1.0–5.0 | 0.5–1.0 | 0.25–1.0 | >5.0 | 0.25–1.0 | >10 | 10–25 | 10–25 | ≦0.25 | ≦0.25 | 0.25–1.0 | >25 | 10–25 |
| 33 | 0.5–1.0 | <0.1 | 1.0–5.0 | >5.0 | 1.0–5.0 | >5.0 | 1.0–5.0 | >10 | >25 | >25 | | | | >25 | >25 |
| 34 | <0.1 | >1.0 | <0.5 | >5.0 | <0.25 | 1.0–5.0 | | 0.5–2.5 | 2.5–10 | >25 | <0.25 | <0.25 | | >25 | >25 |
| 35 | | | | | | | | | 10–25 | 10–25 | | | 1.0–5.0 | 10 | >25 |
| 36 | | | | | | | | | 10–25 | >5.0 | | | >5.0 | 10 | >10 |
| 37 | >1.0 | >1.0 | >5.0 | >5.0 | >5.0 | >5.0 | >5.0 | >10 | >10 | 2.5–10 | | | 2.5–10 | 2.5–10 | >10 |
| 38 | >1.0 | >1.0 | >5.0 | >5.0 | 1.0–5.0 | >5.0 | 1.0–5.0 | >10 | >10 | >10 | 0.25–1.0 | 1.0–5.0 | 1.0–5.0 | >25 | >25 |
| 39 | 0.5–1.0 | <0.1 | 1.0–5.0 | >5.0 | >5.0 | >5.0 | >5.0 | >10 | >10 | >10 | 1.0–5.0 | 0.25–1.0 | >5.0 | >25 | >10 |
| 40 | >1.0 | >1.0 | >5.0 | >25 | >5.0 | >5.0 | >5.0 | >10 | >10 | >10 | <0.25 | 1.0–5.0 | <0.25 | >25 | >10 |
| 41 | <0.1 | <0.1 | <0.5 | 1.0–5.0 | >5.0 | >5.0 | >5.0 | >10 | >10 | 10–25 | <5.0 | >5.0 | >5.0 | >25 | 2.5–10 |
| 42 | <0.1 | 0.1 | >5.0 | >5.0 | | | | | >25 | >25 | | | | >25 | >10 |
| 43 | >1.0 | >1.0 | >5.0 | >5.0 | | | | | >25 | >25 | | | | >25 | >10 |
| 44 | >1.0 | 0.5–1.0 | >5.0 | >5.0 | | | | | >25 | >25 | 0.25–1.0 | 0.25–1.0 | >5.0 | >25 | >10 |
| 45 | >1.0 | >1.0 | >5.0 | >5.0 | | >5.0 | >5.0 | >10 | >10 | ≧10 | | | | >10 | >10 |

TABLE IV-continued

| Compound No. | Egt Prot | Egt Syst | Pr Prot | Pr Syst | Pl Erad | Pl Prot | Pl Syst | Vi Erad | Vi Prot | Vi Syst | Un Erad | Un Prot | Un Syst | Ca Prot | Ca Syst |
|---|---|---|---|---|---|---|---|---|---|---|---|---|---|---|---|
| 46 | >1.0 | >1.0 | *>100 | | | | | >10 | >10 | >10 | | | | 2.5-10 | >10 |
| 47 | >1.0 | >1.0 | *>100 | | | | | >10 | ≧>10 | >10 | | | | >10 | >10 |
| 48 | >0.1 | >1.0 | | *>100 | >5.0 | >5.0 | | | *>100 | | >5.0 | >5.0 | | *>100 | |
| 49 | | | *>100 | | | | | | *>100 | | | | | *>100 | >10 |
| 50 | >1.0 | >1.0 | >5.0 | >5.0 | >5.0 | >5.0 | >5.0 | >10 | >25 | >25 | >5.0 | >5.0 | | >10 | >10 |
| 51 | >12.5 | | *>100 | 1.0-5.0 | | | | | >10 | >25 | | | | *>100 | >10 |
| 52 | >0.5 | >1.0 | >5.0 | >5.0 | >5.0 | >1.0 | >5.0 | >10 | >10 | >10 | <0.25 | >1.0 | >5.0 | >10 | >10 |
| 53 | 0.5-1.0 | >1.0 | | >5.0 | | | | | >10 | >25 | | | | >10 | >10 |
| 54 | 0.1-0.5 | >1.0 | >5.0 | >5.0 | | | | | >25 | >10 | | | | >25 | >10 |
| 55 | >1.0 | >1.0 | >5.0 | >5.0 | | | | >10 | >10 | >10 | | | | >10 | >10 |

*Combined prot/syst test

We claim:

1. A compound selected from the group consisting of (1) compounds of Formula (A):

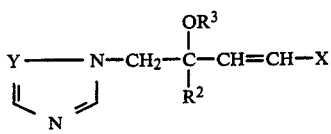

formula A wherein $R^3$ is hydrogen; X is hydrogen, methyl, ethyl or propyl; Y is N and $R^2$ is 2,4-dichlorophenyl; and (2) compounds of Formula (B):

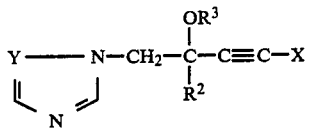

formula B wherein $R^3$ is hydrogen; X is hydrogen, methyl, ethyl or propyl; $R^2$ is 2,4-dichlorophenyl, and Y is N.

2. A compound according to claim 1 wherein the compound is a Formula B compound wherein $R^3$ is H; X is $C_2H_5$; $R^2$ is 2,4-dichloro-phenyl; and Y is N.

3. A compound according to claim 1 wherein the compound is a Formula B compound wherein $R^3$ is H; X is H; $R^2$ is 2,4-dichlorophenyl; and Y is N.

4. A compound according to claim 1 wherein the compound is a Formula B compound wherein $R^3$ is H; X is $CH_3$; $R^2$ is 2,4-dichlorophenyl; and Y is N.

5. A compound according to claim 1 wherein the compound is a Formula A compound wherein $R^3$ is H; X is $C_2H_5$; $R^2$ is 2,4-dichlorophenyl; and Y is N.

6. A compound according to claim 1 wherein the compound is a Formula A compound wherein $R^3$ is H; X is H; $R^2$ is 2,4-dichlorophenyl; and Y is N.

7. A method of combating fungi, which comprises applying to a plant, to seed of a plant, or to the locus of the plant or seed an effective amount of a compound according to claim 1.

8. A method of regulating plant growth, which comprises applying to the plant, to seed of a plant or to the locus of a plant or seed, an effective amount of a compound according to claim 1.

* * * * *